United States Patent
Kawaguchi et al.

(10) Patent No.: US 12,090,133 B2
(45) Date of Patent: Sep. 17, 2024

(54) TOPICAL COMPOSITION

(71) Applicants: The Mentholatum Company, Orchard Park, NY (US); ROHTO Pharmaceutical Co., Ltd., Osaka (JP)

(72) Inventors: Yoshiaki Kawaguchi, Orchard Park, NY (US); Tammam Alama, Osaka (JP)

(73) Assignees: THE MENTHOLATUM COMPANY, Orchard Park, NY (US); ROHTO PHARMACEUTICAL CO., LTD., Osaka (JP)

( * ) Notice: Subject to any disclaimer, the term of this patent is extended or adjusted under 35 U.S.C. 154(b) by 67 days.

(21) Appl. No.: 17/498,147

(22) Filed: Oct. 11, 2021

(65) Prior Publication Data

US 2022/0133677 A1    May 5, 2022

Related U.S. Application Data

(60) Provisional application No. 63/109,947, filed on Nov. 5, 2020.

(51) Int. Cl.
| | |
|---|---|
| *A61K 31/325* | (2006.01) |
| *A61K 9/00* | (2006.01) |
| *A61K 9/06* | (2006.01) |

(52) U.S. Cl.
CPC .......... *A61K 31/325* (2013.01); *A61K 9/0014* (2013.01); *A61K 9/06* (2013.01)

(58) Field of Classification Search
CPC ....... A61K 31/325; A61K 9/0014; A61K 9/06
See application file for complete search history.

(56) References Cited

U.S. PATENT DOCUMENTS

| | | | |
|---|---|---|---|
| 2011/0236321 A1* | 9/2011 | Trumbore | A61K 9/0014 424/45 |
| 2016/0128944 A1* | 5/2016 | Chawrai | A61K 8/466 514/159 |
| 2018/0214472 A1* | 8/2018 | Bapat | A61K 31/496 |

FOREIGN PATENT DOCUMENTS

| | | | |
|---|---|---|---|
| CA | 3122016 A1 | | 6/2020 |
| JP | 2005170913 | * | 6/2005 |
| JP | 2006-232853 A | | 9/2006 |

OTHER PUBLICATIONS

Cosmetic Ingredient Review (2014) (Year: 2014).*
JP2005170913—English translation (Year: 2005).*
OECD/OCDE, "OECD Guideline for the Testing of Chemicals: Skin Absorption: in vitro Method"; Apr. 13, 2004, pp. 1-8.
Kezutyte, et al., Study of Tolnaftate Release from Fatty Acids Containing Ointment and Penetration Into Human Skin Ex Vivo, Acta Polonia Pharmaceutica, ISSN 0001-6837, Nov. 2011, pp. 965-973.
Babu, R., et al., Fatty Alcohols, Fatty Acids, and Fatty Acid Esters as Penetration Enhancers, in Percutaneous Penetration Enhancers Chemical Methods in Penetration Enhancement: Modification of the Stratum Corneum (ed. N. Dragicevic and H.I. Maibach, 2015), pp. 133-150.
Teixeira, R., et al., Lysine-Based Surfactants as Chemical Permeation Enhancers for Dermal Delivery of Local Anesthetics, International Journal of Pharmaceutics, vol. 474, 2014, pp. 212-222.

* cited by examiner

*Primary Examiner* — Umamaheswari Ramachandran
(74) *Attorney, Agent, or Firm* — Pearne & Gordon LLP

(57) ABSTRACT

Problem: To provide a topical composition having excellent permeability in the stratum corneum. Solution: A topical composition is prepared that comprises: (A) one antifungal agent or two or more antifungal agents selected from the group consisting of tolnaftate and pharmaceutically acceptable salts thereof; and (B) at least one compound selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

12 Claims, No Drawings

TOPICAL COMPOSITION

TECHNICAL FIELD

The present invention relates to a topical composition. More specifically, the present invention relates to a topical composition comprising one antifungal agent or two or more antifungal agents selected from the group consisting of tolnaftate and pharmaceutically acceptable salts thereof.

BACKGROUND ART

Antifungal agents used to inhibit the growth of fungi are widely used to treat, prevent, and ameliorate diseases and symptoms caused by fungal infections. External preparations for antifungal use are used in particular to treat skin infections due to ringworms, *cutaneous candida*, and *tinea versicolor* (Patent Document 1).

Fungal infections may occur throughout the skin but especially in thick portions of the stratum corneum such as on the heels, and an appropriate treatment is desired.

CITATION LIST

Patent Literature

Patent Citation 1: JP 2006-232853 A

SUMMARY OF INVENTION

Technical Problem

Antifungal agents that block the growth of fungi are widely used to treat, prevent, and ameliorate diseases and symptoms caused by fungal infections, but topical compositions suitable for use on fungal infections that occur in the skin, and especially in the stratum corneum, have not been sufficiently studied.

In view of these circumstances, it is an object of the present invention to provide a topical composition containing an antifungal agent which improves permeability in the stratum corneum of one antifungal agent or two or more antifungal agents selected from the group consisting of tolnaftate and pharmaceutically acceptable salts thereof.

Technical Solution

The present inventors discovered that the use of both (A) one antifungal agent or two or more antifungal agents selected from the group consisting of tolnaftate and pharmaceutically acceptable salts thereof (also termed "component (A)"), and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters (also termed "component (B)") yielded a topical composition that improved permeability of component (A) in the stratum corneum, and this finding led to the completion of the present invention.

The present invention provides a topical composition comprising: (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

The present invention also provides a method for improving the amount of permeation in the stratum corneum of a subject of (A) one antifungal agent or two or more antifungal agents selected from the group consisting of tolnaftate and pharmaceutically acceptable salts thereof in a composition, the method comprising applying to the stratum corneum of the subject the composition comprising component (A) in the copresence of (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

The present invention also relates to a method for treating a fungal infection of the stratum corneum of a subject in need thereof by applying to the stratum corneum of the subject a topical composition comprising: (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

Advantageous Effects

The present invention provides a topical composition for treating a fungal infection.

DESCRIPTION OF EMBODIMENTS

Topical Composition

The present invention relates to a topical composition comprising. (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

(A) One Antifungal Agent or Two or More Antifungal Agents Selected from the Group Consisting of Tolnaftate and Pharmaceutically Acceptable Salts Thereof One antifungal agent or two or more antifungal agents selected from the group consisting of tolnaftate and pharmaceutically acceptable salts thereof has the function of inhibiting or suppressing the growth of fungi or of killing fungi, and is used to treat, prevent and ameliorate diseases and symptoms caused by fungal infections. There are no particular restrictions on the one antifungal agent or two or more antifungal agents selected from the group consisting of tolnaftate and pharmaceutically acceptable salts thereof as long as it is of a grade used in the field of pharmaceuticals or quasi-drugs as a raw material in external preparations.

From the standpoint of making the effect of the present invention more pronounced, the total amount of (A) one antifungal agent or two or more antifungal agents selected from the group consisting of tolnaftate and pharmaceutically acceptable salts thereof relative to the total mass of the topical composition is preferably 0.01 mass % or more, more preferably 0.03 mass % or more, even more preferably 0.05 mass % or more, still more preferably 0.08 mass % or more, and yet more preferably 0.1 mass %. From the standpoint of making the effect of the present invention more pronounced, the total amount of (A) one antifungal agent or two or more antifungal agents selected from the group consisting of tolnaftate and pharmaceutically acceptable salts thereof relative to the total mass of the topical composition is preferably 10 mass % or less, more preferably 8 mass % or less, even more preferably 7 mass % or less, still more preferably 5 mass % or less, yet more preferably 4 mass % or less, and most preferably equal to or less than 3 mass %. From the standpoint of making the effect of the present invention more pronounced, the total amount of (A) one antifungal agent or two or more antifungal agents selected from the group consisting of tolnaftate and pharmaceutically acceptable salts thereof relative to the total mass of the topical composition is preferably from 0.01 mass % to 10 mass %, more preferably from 0.03 mass % to 8 mass %, even more preferably from 0.05 mass % to 7 mass %, still more preferably from 0.08 mass % to 5 mass %, yet more preferably from 0.09 mass % to 4 mass %, and most preferably from 0.1 mass % to 3 mass %. Among these, 1 mass % is most preferred.

(B) One Compound or Two or More Compound Selected from the Group Consisting of Ester Compounds of Fat Acids Having, from 8 to 18 Carbon Atoms and Dihydric Alcohols Having from 2 to 4 Carbon Atoms, Lysine Acyl Glutamate, Lysine Diacyl Glutamate, Pharmaceutically Acceptable Salts of Lysine Acyl Glutamate or Lysine Diacyl Glutamate, Diethylene Glycol-Based Glycol Ethers, Cyclohexanedicarboxylic Acid Polyoxyethylene Alkyl Ethers, Mannosylerythritol Lipids, and Sucrose Fatty Acid Esters (B-1) One Compound or Two or More Compounds Selected from the Group Consisting of Ester Compounds of Fatty Acids Having from 8 to 18 Carbon Atoms and Dihydric Alcohols Having from 2 to 4 Carbon Atoms, as Well as Lysine Acyl Glutamates, Lysine Diacyl Glutamates, and Pharmaceutically Acceptable Salts Thereof In one aspect of the present invention, component (B) is preferably (B-1) one compound or two or more compounds selected from the group consisting of ester compounds of fatty acids having from 8 to 18 carbon atoms and dihydric alcohols having from 2 to 4 carbon atoms, as well as lysine acyl glutamates, lysine diacyl glutamates, and pharmaceutically acceptable salts thereof (also termed "compound (B-1)").

Here, the ester compound of fatty acids having from 8 to 18 carbon atoms and dihydric alcohols having from 2 to 4 carbon atoms is preferably propylene glycol monocaprylate, propylene glycol dicaprylate, propylene glycol didecanoate, diglyceryl triisostearate, propylene glycol dicaprate, pentaerythritol tetra-2-ethylhexanoate, trimethylolpropane tri-2-ethylhexanoate, trimethylolpropane triisostearate, tri (capryl/capric acid) glyceryl, or 2-butyl-2-ethyl 2-ethylhexanoate-1,3-propanediol, more preferably propylene glycol monocaprylate, propylene glycol dicaprylate, or propylene glycol didecanoate, and even more preferably propylene glycol monocaprylate.

The lysine acyl glutamate or lysine diacyl glutamate is preferably a lysine diacyl glutamate whose acyl group is derived from a fatty acid, more preferably lysine dilauroyl glutamate, lysine dimyristoyl glutamate, lysine distearoyl glutamate, or lysine dilinoleyl glutamate, and even more preferably lysine dilauroyl glutamate. Pharmaceutically acceptable salts of these include alkali metal salts such as a sodium salt or potassium salt, an organic amine salt such as a triethanolamine salt, and basic amino acid salts such as arginine. Alkali metal salts are preferred, and a sodium salt is more preferred. Among lysine acyl glutamates, lysine diacyl glutamates, and pharmaceutically acceptable salts thereof, sodium lysine dilauroyl glutamate is preferred.

One of these compounds or a suitable combination of two or more of these compounds can be used as component (B-1).

(B-2) One Compound or Two or More Compounds Selected from the Group Consisting of Diethylene Glycol-Based Glycol Ethers, Cyclohexanedicarboxylic Acid Polyoxethylene Alkyl Ethers, Mannosylerythritol Lipids, and Sucrose Fatty Acid Esters In one aspect of the present invention, component (B) is preferably (B-2) one compound or two or more compounds selected from the group consisting of diethylene glycol-based glycol ethers, cyclohexanedicarboxylic acid polyoxyethylene alkyl ethers, mannosylerythritol lipids, and sucrose fatty acid esters (also termed "compound (B-2)").

Examples of diethylene glycol-based glycol ethers include diethylene glycol monomethyl ether, diethylene glycol monoethyl ether, and diethylene glycol monopropyl ether. Diethylene glycol monoethyl ether is preferred.

The cyclohexanedicarboxylic acid polyoxyethylene alkyl ether may be, for example, a diester compound of a dicarboxylic acid and a polyoxyalkylene alkyl ether. Examples of dicarboxylic acids used here include oxalic acid, malonic acid, succinic acid, tartaric acid, malic acid, glutaric acid, adipic acid, pimaric acid, suberic acid, azelaic acid, sebacic acid, aspartic acid, glutamic acid, acetonedicarboxylic acid, phthalic acid, and 1,4-cyclohexanedicarboxylic acid. Examples of polyoxyalkylene alkyl ethers include polyoxyethylene monoalkyl ethers. Diethylene glycol monoethyl ether and triethylene glycol monoethyl ether are preferred. Among examples of cyclohexanedicarboxylic acid polyoxyethylene alkyl ethers, bis-ethoxydiglycol cyclohexanedicarboxylate is preferred.

Examples of sucrose fatty acid esters include sucrose lauric acid esters, sucrose myristic acid esters, sucrose palmitic acid esters, sucrose stearic acid esters, and sucrose oleic acid esters. Sucrose lauric acid esters are preferred. There are no particular restrictions on the HLB of the sucrose fatty acid esters. However, it can be from 1 to 20, preferably from 1 to 10, more preferably from 1 to 5, and most preferably from 3 to 5.

One of these compounds or a suitable combination of two or more of these compounds can be used as component (B-2).

There are no particular restrictions on any example of component (B) as long as it is of a grade used in the field of pharmaceuticals or quasi-drugs as a raw material in external preparations. Each example of component (B) can be synthesized or a commercially available product can be used. For component (B), any one type of component (B-1) or (B-2) can be used alone. Also, any combination of two or more types of component (B-1) or (B-2) or component (B-1) and (B-2) can be used.

From the standpoint of making the effect of the present invention more pronounced, the total amount of component (B) relative to the total mass of the topical composition is preferably 0.01 mass % or more, more preferably 0.02 mass % or more, even more preferably 0.03 mass % or more, still more preferably 0.05 mass % or more, and yet more preferably 0.1 mass % or more. From the standpoint of usability and handling of the formulation, the total amount of component (B) relative to the total mass of the topical composition is preferably 20 mass % or less, more preferably 18 mass % or less, even more preferably 15 mass % or less, and still more preferably 10 mass % or less. From the standpoint of making the effect of the present invention more pronounced, the total amount of component (B) relative to the total mass of the topical composition is preferably from 0.01 to 20 mass %, more preferably from 0.02 to 18 mass %, even more preferably from 0.03 to 15 mass %, and still more preferably from 0.1 to 10 mass %.

From the standpoint of making the effect of the present invention more pronounced, the ratio of component (B) to component (A) in a topical composition of the present invention, for example, the amount of component (B) per 1 part by mass of component (A), is preferably from 0.001 to 200 parts by mass, more preferably from 0.002 to 180 parts by mass, even more preferably from 0.003 to 150 parts by mass, and still more preferably from 0.005 to 120 parts by mass.

From the standpoint of making the effect of the present invention more pronounced, the total amount of component (B-1) relative to the total mass of the topical composition is preferably 0.001 mass % or more, more preferably 0.003 mass % or more, even more preferably 0.005 mass % or more, and still more preferably 0.01 mass % or more. From the standpoint of usability and handling of the formulation, the total amount of component (B-1) relative to the total mass of the topical composition is preferably 20 mass % or less, more preferably 18 mass % or less, even more preferably 15 mass % or less, and still more preferably 10 mass % or less. From the standpoint of making the effect of the present invention more pronounced, the total amount of component (B-1) relative to the total mass of the topical composition is usually from 0.001 to 20 mass %, preferably from 0.003 to 18 mass %, more preferably from 0.005 to 15 mass %, even more preferably from 0.008 to 13 mass %, and still more preferably from 0.01 to 10 mass %.

From the standpoint of making the effect of the present invention more pronounced, the ratio of component (B-1) to component (A) in a topical composition of the present invention, for example, the amount of component (B-1) per 1 part by mass of component (A), is preferably from 0.001 to 200 parts by mass, more preferably from 0.002 to 180 parts by mass, even more preferably from 0.0025 to 150 parts by mass, still more preferably from 0.003 to 120 parts by mass, and yet more preferably from 0.004 to 100 parts by mass.

From the standpoint of making the effect of the present invention more pronounced, the total amount of component (B-2) relative to the total mass of the topical composition is preferably 0.01 mass % or more, more preferably 0.03 mass % or more, even more preferably 0.05 mass % or more, and still more preferably 0.1 mass/o or more. From the standpoint of usability and handling of the formulation, the total amount of component (B) relative to the total mass of the topical composition is preferably 20 mass % or less, more preferably 18 mass % or less, even more preferably 15 mass % or less, and still more preferably 10 mass % or less. From the standpoint of making the effect of the present invention more pronounced, the total amount of component (B-2) relative to the total mass of the topical composition is usually from 0.01 to 20 mass %, preferably from 0.03 to 18 mass %, more preferably from 0.05 to 15 mass %, even more preferably from 0.08 to 13 mass %, and still more preferably from 0.1 to 10 mass %.

From the standpoint of making the effect of the present invention more pronounced, the ratio of component (B-2) to component (A) in a topical composition of the present invention, for example, the amount of component (B-2) per 1 part by mass of component (A), is preferably from 0.01 to 200 parts by mass, more preferably from 0.015 to 180 parts by mass, even more preferably from 0.02 to 150 parts by mass, still more preferably from 0.025 to 130 parts by mass, yet more preferably from 0.03 to 120 parts by mass, still yet more preferably from 0.04 to 110 parts by mass, and most preferably from 0.05 to 100 parts by mass.

When, for example, component (B) is an ester compound of a fatty acid having from 8 to 18 carbon atoms and a dihydric alcohol having from 2 to 4 carbon atoms, from the standpoint of making the effect of the present invention more pronounced, the amount relative to the total mass of the topical composition is preferably from 0.01 to 20 mass %, more preferably from 0.05 to 15 mass %, and even more preferably from 0.1 to 10 mass %. From the standpoint of making the effect of the present invention more pronounced, the ratio of ester compound of a fatty acid having from 8 to 18 carbon atoms and a dihydric alcohol having from 2 to 4 carbon atoms to component (A) in a topical composition of the present invention, that is, the amount per 1 part by mass of component (A), is preferably from 0.01 to 20 parts by mass, more preferably from 0.02 to 15 parts by mass, and even more preferably from 0.03 to 10 parts by mass.

When, for example, component (B) is one compound or two or more compounds selected from the group consisting of lysine acyl glutamates, lysine diacyl glutamates, and pharmaceutically acceptable salts thereof, from the standpoint of making the effect of the present invention more pronounced, the amount relative to the total mass of the topical composition is preferably from 0.001 to 10 mass %, more preferably from 0.005 to 5 mass %, and even more preferably from 0.01 to 1 mass %. From the standpoint of making the effect of the present invention more pronounced, the ratio of one compound or two or more compounds selected from the group consisting of lysine acyl glutamates, lysine diacyl glutamates, and pharmaceutically acceptable salts thereof to component (A) in a topical composition of the present invention, that is, the amount per 1 part by mass of component (A), is preferably from 0.001 to 10 parts by mass, more preferably from 0.002 to 5 parts by mass, and even more preferably from 0.003 to 1 part by mass.

When, for example, component (B) is a diethylene glycol-based glycol ether, from the standpoint of making the effect of the present invention more pronounced, the amount relative to the total mass of the topical composition is preferably from 0.01 to 20 mass %, more preferably from 0.03 to 18 mass %, even more preferably from 0.05 to 15 mass %, and still more preferably from 0.1 to 10 mass %. From the standpoint of making the effect of the present invention more pronounced, the ratio of diethylene glycol-based glycol ether to component (A) in a topical composition of the present invention, that is, the amount per 1 part by mass of component (A), is preferably from 0.01 to 200 parts by mass, more preferably from 0.02 to 180 parts by mass, even more preferably from 0.025 to 150 parts by mass, and still more preferably 0.03 to 100 parts by mass.

When, for example, component (B) is a cyclohexanedicarboxylic acid polyoxyethylene alkyl ether, from the standpoint of making the effect of the present invention more pronounced, the amount relative to the total mass of the topical composition is preferably from 0.01 to 20 mass %, more preferably from 0.05 to 18 mass %, even more preferably from 0.08 to 15 mass %, and still more preferably 0.1 to 10 mass %. From the standpoint of making the effect of the present invention more pronounced, the ratio of cyclohexanedicarboxylic acid polyoxyethylene alkyl ether to component (A) in a topical composition of the present invention, that is, the amount per 1 part by mass of component (A), is preferably from 0.01 to 200 parts by mass, more preferably from 0.02 to 180 parts by mass, even more preferably from 0.025 to 150 parts by mass, and still more preferably from 0.03 to 100 parts by mass.

When, for example, component (B) is a mannosylerythritol lipid, from the standpoint of making the effect of the present invention more pronounced, the amount relative to the total mass of the topical composition is preferably from 0.001 to 10 mass %, more preferably from 0.005 to 8 mass %, even more preferably from 0.007 to 5 mass %, and still more preferably from 0.01 to 1 mass %. From the standpoint of making the effect of the present invention more pronounced, the ratio of mannosylerythritol lipid to component (A) in a topical composition of the present invention, that is, the amount per 1 part by mass of component (A), is preferably from 0.01 to 200 parts by mass, more preferably from 0.02 to 150 parts by mass, even more preferably from 0.025 to 130 parts by mass, and still more preferably from 0.03 to 100 parts by mass.

When, for example, component (B) is a sucrose fatty acid ester, from the standpoint of making the effect of the present invention more pronounced, the amount relative to the total mass of the topical composition is preferably from 0.01 to 10 mass %, more preferably from 0.03 to 8 mass %, still more preferably from 0.05 to 5 mass %, and even more preferably from 0.1 to 3 mass %. From the standpoint of making the effect of the present invention more pronounced, the ratio of sucrose fatty acid ester to component (A) in a topical composition of the present invention, that is, the amount per 1 part by mass of component (A), is preferably from 0.01 to 100 parts by mass, more preferably from 0.02 to 70 parts by mass, even more preferably from 0.025 to 50 parts by mass, and still more preferably from 0.03 to 30 parts by mass.

(C) Urea

A topical composition of the present invention may optionally contain (C) urea (also termed "component (C)") in addition to components (A) and (B).

There are no particular restrictions on the (C) urea used in the present invention as long as it is of a grade used in the field of pharmaceuticals or quasi-drugs as a raw material in external preparations.

From the standpoint of making the effect of the present invention more pronounced, the total amount of component (C) relative to the total mass of the topical composition is preferably 0.1 mass % or more, more preferably 0.5 mass % or more, even more preferably 1 mass % or more, and still more preferably 2 mass % or more. From the standpoint of making the effect of the present invention more pronounced, the total amount of component (C) relative to the total mass of the topical composition is preferably 40 mass % or less, more preferably 30 mass % or less, even more preferably 25 mass % or less, and still more preferably 20 mass % or less. From the standpoint of making the effect of the present invention more pronounced, the total amount of component (C) relative to the total mass of the topical composition is preferably from 0.1 to 40 mass %, more preferably from 0.5 to 30 mass %, even more preferably from 1 to 25 mass %, and still more preferably from 2 to 20 mass %.

From the standpoint of making the effect of the present invention more pronounced, the ratio of component (C) to component (A) in a topical composition of the present invention, for example, the amount of component (C) per 1 part by mass of component (A), is preferably from 0.1 to 200 parts by mass, more preferably from 0.2 to 190 parts by mass, even more preferably from 0.5 to 180 parts by mass, and still more preferably from 0.7 to 170 parts by mass.

(D) Dicarboxylic Acid Esters

A topical composition of the present invention may optionally contain a dicarboxylic acid ester (D) (also termed "component (D)") in addition to components (A) and (B). There are no particular restrictions on the dicarboxylic acid ester (D) used in the present invention as long as it is of a grade used in the field of pharmaceuticals or quasi-drugs as a raw material in external preparations. The dicarboxylic acid ester (D) is preferably diisopropyl adipate, diethyl sebacate, diisopropyl sebacate, dimethyl succinate, dibutyl adipate, diisobutyl adipate, dioctyl adipate, dioctyl sebacate, diethyl phthalate, and/or dibutyl phthalate, more preferably diisopropyl adipate, diethyl sebacate and/or diisopropyl sebacate, and even more preferably diethyl sebacate.

From the standpoint of making the effect of the present invention more pronounced, the total amount of component (D) relative to the total mass of the topical composition is preferably 0.01 mass % or more, more preferably 0.02 mass % or more, even more preferably 0.05 mass % or more, and still more preferably 0.1 mass % or more. From the standpoint of making the effect of the present invention more pronounced, the total amount of component (D) relative to the total mass of the topical composition is preferably 40 mass % or less, more preferably 30 mass % or less, even more preferably 25 mass % or less, and still more preferably 20 mass % or less. From the standpoint of making the effect of the present invention more pronounced, the total amount of component (D) relative to the total mass of the topical composition is preferably from 0.01 to 40 mass %, more preferably from 0.02 to 30 mass %, even more preferably from 0.05 to 25 mass %, and still more preferably from 0.1 to 20 mass %.

From the standpoint of making the effect of the present invention more pronounced, the ratio of component (D) to component (A) in a topical composition of the present invention, for example, the amount of component (D) per 1 part by mass of component (A), is preferably from 0.01 to 200 parts by mass, more preferably from 0.02 to 180 parts by mass, even more preferably from 0.025 to 150 parts by mass, and still more preferably from 0.03 to 100 parts by mass.

(E) Water

A topical composition of the present invention may be an aqueous composition containing water (E) (also termed "component (E)") in addition to components (A) and (B). From the standpoint of usability and handling of a formulation of a topical composition of the present invention, the total amount of component (E) relative to the total mass of the topical composition is preferably 10 mass % or more, more preferably 15 mass % or more, even more preferably 20 mass % or more, and still more preferably 30 mass % or more. From the standpoint of making the effect of the present invention more pronounced, the total amount of component (E) relative to the total mass of the topical composition is preferably 80 mass % or less, more preferably 75 mass % or less, even more preferably 70 mass % or less, and still more preferably 65 mass % or less. The amount of component (E) relative to the total mass of the topical composition is preferably from 10 to 80 mass %, more preferably from 15 to 75 mass %, even more preferably from 20 to 70 mass %, and still more preferably from 30 to 65 mass %.

However, aspects of the present invention containing no water may also be preferred.

A topical composition of the present invention may optionally contain a polyhydric alcohol in addition to components (A) and (B). Examples of polyhydric alcohols include polyethylene glycol, polyvinyl alcohol, propylene glycol, 1,3-butylene glycol, glycerin, diglycerin, dipropylene glycol, 3-methyl-1,3-butanediol, and isoprene glycol. Polyethylene glycol, glycerin, or 1,3-butylene glycol is preferred.

From the standpoint of making the effect of the present invention more pronounced, the total amount of polyhydric alcohol relative to the total mass of the topical composition is preferably 0.5 mass % or more, more preferably 1 mass % or more, even more preferably 2 mass % or more, and still more preferably 3 mass % or more. From the standpoint of making the effect of the present invention more pronounced, the total amount of polyhydric alcohol relative to the total mass of the topical composition is preferably 20 mass % or less, more preferably 18 mass % or less, even more preferably 15 mass % or less, and still more preferably 10 mass % or less. The total amount of polyhydric alcohol relative to the total mass of the topical composition is preferably from 0.5 to 20 mass %, more preferably from 1 to 18 mass %, even more preferably from 2 to 15 mass %, and still more preferably from 3 to 10 mass %.

From the standpoint of making the effect of the present invention more pronounced, the ratio of polyhydric alcohol to component (A) in a topical composition of the present invention, that is, the amount per 1 part by mass of component (A), is preferably from 0.1 to 200 parts by mass, more preferably from 0.2 to 180 parts by mass, even more preferably from 0.5 to 150 parts by mass, and still more preferably from 1 to 100 parts by mass.

Examples of nonionic surfactants include sorbitan fatty acid esters, propylene glycol fatty acid esters, castor oil derivatives, polyoxyethylene sorbitan fatty acid esters, polyoxyalkylene alkyl ethers, glycerin fatty acids, amines, silicone-based surfactants, and polyoxyethylene lauryl alcohol ethers. Examples of the sorbitan fatty acid esters include sorbitan monoisostearate, sorbitan monolaurate, sorbitan monopalmitate, sorbitan monostearate, penta-2-ethylhexylate diglycerol sorbitan, tetra-2-ethylhexylate diglycerol sorbitan, and sorbitan sesquioleic acid esters. Examples of the propylene glycol fatty acid esters include propylene glycol fatty acid esters such as propylene glycol monostearate. Examples of castor oil derivatives include polyoxyethylene castor oil and hardened polyoxyethylene castor oil. Examples of polyoxyethylene sorbitan fatty acid esters include polyoxyethylene monolaurate (20) sorbitan (polysorbate 20), polyoxyethylene monostearate (20) sorbitan (polysorbate 60), polyoxyethylene monooleate (20) sorbitan (polysorbate 80), and polyoxyethylene isostearate (20) sorbitan. Examples of polyoxyalkylene alkyl ethers include coconut oil fatty acid polyoxyethylene glyceryl monoesters, glycerin alkyl ethers, alkyl glucosides, and polyoxyethylene cetyl ether. Examples of glycerin fatty acids include glyceryl monostearate and glycerin malic acid monostearate. Examples of amines include stearylamines and oleylamines. Examples of silicone-based surfactants include polyoxyethylene/methylpolysiloxane copolymers, lauryl PEG-9 polydimethylsiloxyethyl dimethicone, and PEG-9 polydimethylsiloxyethyl dimethicone.

The nonionic surfactants are preferably polysorbate fatty acid esters, castor oil derivatives, polyoxyethylene sorbitan fatty acid esters, and/or glycerin fatty acids. Hardened polyoxyethylene castor oil is especially preferred.

From the standpoint of making the effect of the present invention more pronounced, the total amount of nonionic surfactant relative to the total mass of the topical composition is preferably from 0.01 to 10 mass % and more preferably from 0.1 to 5 mass %. From the standpoint of making the effect of the present invention more pronounced, the ratio of nonionic surfactant to component (A) in a topical composition of the present invention, for example, the amount of nonionic surfactant per 1 part by mass of component (A), is preferably from 0.01 to 10 parts by mass and more preferably from 0.1 to 5 parts by mass.

Pharmaceutically Acceptable Salts

In the present specification, a "pharmaceutically acceptable salt" can be an organic salt or inorganic salt. Examples of organic salts include ammoniums, diethanolamines, triethanolamines, and ethylenediamine. Examples of inorganic salts include salts with sodium, potassium, calcium, and magnesium. Specific examples include salts of inorganic acids such as hydrochloric acid, hydrobromic acid, sulfuric acid, nitric acid, and phosphoric acid; salts of organic acids such as methanesulfonic acid, benzenesulfonic acid, para-toluenesulfonic acid, acetic acid, propionic acid, tartaric acid, fumaric acid, maleic acid, malic acid, oxalic acid, succinic acid, citric acid, benzoic acid, mandelic acid, silicic acid, lactic acid, glycolic acid, glucuronic acid, ascorbic acid, succinic acid, and salicylic acid; and salts with acidic amino acids such as aspartic acid and glutamic acid. Note that "salt" includes solvates and hydrates of salts. There are no particular restrictions on the form of the salt in component (A) but, from the standpoint of availability, a salt of an inorganic acid is preferred, and a hydrochloride or a nitrate is especially preferred.

Bases, Carriers, and Other Components

A topical composition of the present invention can contain a well-known base or carrier that can be used in a drug or quasi-drug within a range that does not impair the effect of the present invention. Other additives that can be used in a topical composition of the present invention include anionic surfactants, amphoteric surfactants, oils, alcohols, preservatives, oxidation inhibitors and antioxidants, cooling agents, polymers, preservatives, chelating agents, pH regulators, stabilizers, dissolution aids, suspending agents, tonicity agents, buffering agents, colorants, fragrances, pigments, and lubricants. One type of additive can be used alone or a combination of two or more types of additives can be used.

Examples of bases or carriers include hydrocarbons, silicone oils, and esters. Examples of hydrocarbons include liquid paraffin, squalane, gelled hydrocarbons (such as Plastibase), ozokelite, α-olefin oligomers, and light liquid paraffin. Examples of silicone oils include methylpolysiloxane, cross-linked methylpolysiloxane, highly polymerized methylpolysiloxane, cyclic silicone, alkyl-modified silicone, cross-linked alkyl-modified silicone, amino-modified silicone, polyether-modified silicone, polyglycerin-modified silicone, cross-linked polyether-modified silicone, cross-linked alkyl polyether-modified silicone, silicone-alkyl chain co-modified/polyether-modified silicone, silicone-alkyl chain co-modified/polyglycerin-modified silicone, polyether-modified branched silicone, polyglycerin modified branched silicone, acrylic silicone, phenyl modified silicone, and silicone resin. Examples of esters include isopropyl myristate, octyldodecyl myristate, isopropyl palmitate, cetyl palmitate, isononyl isononanoate, and pentaerythritol tetra (2-ethylhexanoate).

One of these bases or carriers or a suitable combination of two or more of these bases or carriers can be used.

Examples of anionic surfactants include lauric acid salts, palmitic acid salts, cocoyl glutamic acid salts, coconut oil methylalanine salts, acylmethyltaurine salts, and polyoxyethylene lauric acid salts. Examples of amphoteric surfactants include lauryl diaminoethyl glycine salts and coconut oil fatty acid betaine salts.

Examples of oils include natural animal and vegetable oils and fats, hydrocarbon oils, ester oils, silicone oils, mineral oils, higher alcohols, higher fatty acids, animal and plant-based essential oils, and synthetic essential oils.

Examples of alcohols include ethanol and isopropanol.

Examples of natural animal and vegetable oils and fats include avocado oil, flaxseed oil, almond oil, olive oil, cacao oil, beef fat, millet oil, wheat germ oil, sesame oil, rice germ oil, rice bran oil, safflower oil, soybean oil, evening primrose oil, camellia oil, corn oil, rapeseed oil, horse fat, persic oil, palm oil, palm kernel oil, sunflower oil, pork fat, grape oil, jojoba oil, macadamia nut oil, mink oil, cottonseed oil, Japan wax, beeswax, salmon oil, palm oil, hardened coconut oil, peanut oil, lanolin, egg yolk oil, and rose hip oil.

Examples of hydrocarbon oils include paraffin-based hydrocarbons and olefin-based hydrocarbons. Specific examples include squalane, squalene, selectin, paraffin, pristane, microcrystalline wax, liquid paraffin, and petrolatum.

Examples of ester oils include synthetic esters and esters of higher alcohols and higher fatty acids. Specific examples include medium-chain fatty acid triglycerides, 2-hexyldecyl adipic acid, di-2-heptylundecyl adipate, isostearyl isostearate, trimethylolpropane triisostearate, cetyl 2-ethylhexanoate, neopentyl glycol di-2-ethylhexanoate, trimethylolpropane tri-2-ethylhexanoate, pentaerythritol tetra-2-ethylhexanoate, cetyl octanate, oleyl oleate, octyldodecyl oleate, decyl oleate, neopentyl glycol dicaprate, 2-ethylhexyl succinate, isocetyl stearate, butyl stearate, cetyl lactate, tetradecyl lactate, isopropyl myristate, octyldodecyl myristate, cetyl myristate, myristyl myristate, octyl palmitate, 2-ethylhexyl palmitate, 2-hexyldecyl palmitate, 2-heptylundecyl palmitate, cholesteryl 12-hydroxystearate, phytosteryl oleate, diisostearyl malate, paramethoxycinnamate ester, and pentaerythrityl tetrarosinate.

Examples of silicone oils include dimethylpolysiloxane, highly polymerized methylpolysiloxane, methylphenylpolysiloxane, methylhydrogenpolysiloxane, octamethylcyclotetrasiloxane, octamethylcyclopentasiloxane, decamethylcyclohexanesiloxane, higher alkoxy-modified silicones such as stearoxy silicones, alkylated silicones, and higher fatty acid ester-modified silicones.

Examples of higher alcohols include cetanol, stearyl alcohol, cetostearyl alcohol, and oleyl alcohol.

Examples of higher fatty acids include saturated or unsaturated linear or branched fatty acids having from 12 to 22 carbon atoms. Specific examples include isostearic acid, oxystearic acid, oleic acid, stearic acid, palmitic acid, behenic acid, myristic acid, lauric acid, lanolic acid, linoleic acid, and linolenic acid.

Preferred examples of preservatives include benzoic acid, acetic acid, phenol, iodine tincture, paraoxybenzoic acid esters, chlorobutanol, chlorocresol, benzyl alcohol, phenethyl alcohol, and dehydroacetic acid.

Examples of oxidation inhibitors include sulfites and ascorbic acid.

Examples of antioxidants include dibutylhydroxytoluene (BHT), butylatedhydroxyanisole (BHA), sodium sulfite, erythorbic acid, L-cysteine hydrochloride, vitamin C, and vitamin E. Examples of vitamin C include ascorbogen-A, ascorbic acid/stearic acid esters, ascorbic acid/palmitic acid esters, L-ascorbyl dipalmitate, ascorbic acid, sodium ascorbate, dehydroascorbic acid, sodium ascorbyl phosphate, ascorbic acid/phosphoric acid sodium salts, and ascorbic acid/phosphoric acid magnesium esters. Examples of vitamin E include dl-α-tocopherol, dl-α-tocopherol acetate, dl-α-tocopherol succinate, and dl-α-tocopherol calcium succinate.

Examples of cooling agents include menthols (such as l-menthol and dl-menthol), camphor (such as d-camphor and dl-camphor), terpenoids such as borneol, essential oils containing terpenoids (such as mint oil), and pharmacologically acceptable salts thereof. One of these agents or a suitable combination of two or more of these agents can be used.

Examples of polymers include cellulose-based polymers, vinyl-based polymers, acrylic polymers, thickening polysaccharides, starch-based polymers, dextran, dextrin fatty acid esters, pectin, casein, dimethyl distearyl ammonium hectorite, (acryloyl dimethyl taurine ammonium/vinylpyrrolidone) copolymers, polyethylene glycol distearate, ethylene glycol triisostearate, polyoxyethylene triisostearate (20) methyl glucoside, bentonite, hectorite, alginic acid and/or pharmaceutically acceptable salts thereof, propylene glycol alginate, and polyethylene glycol.

Examples of cellulose-based polymers include sodium carboxymethyl cellulose, methyl cellulose, hydroxymethyl cellulose, hydroxyethyl cellulose, hydroxypropyl cellulose, and hydroxypropyl methyl cellulose. One type or two or more types of these polymers can be used.

Examples of vinyl-based polymers include polyvinylpyrrolidone, polyvinyl alcohol, and polyvinylmethyl ether. One type or two or more types of these polymers can be used.

Examples of acrylic polymers include acrylic acid/alkyl methacrylate copolymers, hydroxyethyl acrylate/acryloyldimethyltaurine salt copolymers (especially hydroxyethyl acrylate/acryloyldimethyltaurine sodium copolymers), sodium acrylate/acryloyl dimethyl taurine copolymers, sodium acrylate/sodium (meth) acrylate/alkyl methacrylate copolymers, Steareth-10 allyl ether/acrylate copolymers, polyacrylic acid or a pharmaceutically acceptable salt thereof (carboxyvinyl polymer), acryloyl dimethyl taurine ammonium copolymer, acrylic acid/methacrylic acid polyoxyethylene glycol ether copolymers, polyacrylamide, and acrylamide/ammonium acrylate copolymers.

Specific examples of thickening polysaccharides used as components in external preparations in the field of pharmaceuticals and quasi-drugs include carrageenan, xanthan gum, gum arabic, pectin, and mucopolysaccharides. Examples of mucopolysaccharides include chondroitin sulfates (such as sodium salts), hyaluronic acid or pharmaceutically acceptable salts thereof (such as sodium salts), hyaluronic acid derivatives or pharmaceutically acceptable salts thereof, heparin, and glycosaminoglycans such as heparinoids.

Examples of starch-based polymers include hydroxypropyl starch phosphate (such as Structure XL from National Starch, LLC), denatured cornstarch, and cornstarch (maize starch).

Examples of preservatives include isobutyl benzoate, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate, and phenoxyethanol.

Examples of chelating agents include EDTA disodium salt and calcium EDTA disodium salt.

Examples of pH regulators include inorganic acids (such as hydrochloric acid and sulfuric acid), organic acids (such as lactic acid, sodium lactate, citric acid, sodium citrate, succinic acid, and sodium succinate), inorganic bases (such as potassium hydroxide and sodium hydroxide), and organic bases (such as triethanolamine, diisopropanolamine, and triisopropanolamine).

Examples of stabilizers include sodium polyacrylate, dibutylhydroxytoluene (BHT), and butylatedhydroxyanisole (BHA).

Examples of dissolution aids include polyethylene glycol, propylene glycol, D-mannitol, benzyl benzoate, trisaminomethane, cholesterol, triethanolamine, sodium carbonate, and sodium citrate.

Examples of suspending agents include surfactants such as stearyl triethanolamine, sodium lauryl sulfate, lauryl aminopropionate, lecithin, soy lecithin, and glycerin monostearate.

Examples of tonicity agent include sodium chloride, glycerin, and D-mannitol.

Examples of buffering agents include buffer solutions with phosphoric acid salts, acetic acid salts, carbonic acid salts, and citric acid salts.

Examples of colorants include inorganic pigments and natural pigments. Examples of lubricants include carnauba wax, hydrous silicon dioxide, sucrose fatty acid esters, silicone resins, magnesium stearate, Setal, and talc.

A topical composition of the present invention can contain other active ingredients in a range that does not impair the effect of the present invention. Specific examples of these active ingredients include local anesthetics, anti-inflammatory agents, bactericidal agents, antihistamines, antipruritic components, moisturizing components, blood circulation promoting components, astringent components, peptides or derivatives thereof, amino acids or derivatives thereof, cell activating components, and vitamins.

pH

There are no particular restrictions on the pH of a topical composition of the present invention as long as it is set properly and within a biologically and chemically acceptable range. However, from the standpoint of safety, the pH can be from 2 to 10, preferably from 3 to 9.5, and more preferably from 5 to 9.

Hardness

There are no particular restrictions on the hardness of a topical composition of the present invention as long as it is set properly and within a biologically and chemically acceptable range. However, from the standpoint of safety, the hardness can be from 20 to 200 g, and preferably from 20 to 100 g.

Form

A topical composition of the present invention can be provided in any form widely used by pharmaceuticals and quasi drugs. Preferably, it is provided in the form of a preparation that can be used as an external preparation on skin. A topical composition of the present invention can assume any form common in the art and there are no particular restrictions. However, from the standpoint of making the effect of the present invention more pronounced, it is preferably provided in the form of an external preparation such as a liquid, suspension, emulsion, gel, lotion, aerosol, mist, spray, solid, or cream. A liquid, suspension, cream, gel, or aerosol is especially preferred.

Formulations can be prepared by mixing the components together according to or in accordance with Remington, 22nd Edition.

Applications

There are no particular restrictions, but a topical composition of the present invention is preferably used to treat athlete's foot, ringworm, and candidiasis, etc. A topical composition of the present invention can also be used on skin on the feet or the entire body, or on hair and nails. However, from the standpoint of making the effect of the present invention more pronounced, it is applied to athlete's foot sites, preferably on the soles of the feet and more preferably on the heels where the stratum corneum tends to be thicker.

Athlete's foot is a skin disease caused by *Trichophyton*. Symptoms include itching, small bumps, peeling, dryness, swelling, hardening, flaking, and roughness. Ringworm is and easily proliferates in the stratum corneum, and athlete's foot symptoms may appear especially on heels where the stratum corneum readily thickens.

Ringworm is also a skin disease caused by *Trichophyton*. Small red rings form on the skin, and symptoms spread gradually. The itchiness is similar to athlete's foot, but ringworm tends to form in thin skin.

Candidiasis is caused by *Candida albicans*, and symptoms include rough skin on the surface of the hands, peeling of skin between the fingers, and white discoloration at the base of the nails.

A topical composition of the present invention can be used to treat symptoms caused by *Trichophyton, tinea versicolor*, candidiasis, interdigital erosion, and candidal intertrigo.

The method of using a topical composition of the present invention depends on factors such as the condition of the skin and stratum corneum, and the age and gender of the patient. However, the following method may be used. A suitable amount (such as about 0.5 to 2 g) may be applied several times a day (about 1 to 5 times, preferably 1 to 3 times, and more preferably 1 time). The composition may be applied so that the daily amount of tolnaftate or pharmaceutically acceptable salt thereof used is, for example, about 5 to 20 mg. The application method depends on the form but coating is preferred. The application period is preferably, for example, 2 to 4 weeks.

Container

There are no particular restrictions on the container for a topical composition of the present invention. It may be any container used as a container for topical drugs, quasi-drugs, and cosmetics. The container can consist of at least one type of container material covering some or all of the surface, preferably all of the surface, coming into contact with the pharmaceutical composition selected from the group consisting of polyolefin resins, acrylic acid resins, polyester, polycarbonate, fluororesin, polyvinyl chloride, polyamide, ABS resin, AS resin, polyacetal, modified polyphenylene ether, polyarylate, polysulfone, polyimide, cellulose acetate, aluminum, and glass.

From the standpoint of easy handling of the formulation, the material covering some or all of the surface coming into contact with the pharmaceutical composition in the container for a topical composition of the present invention is preferably a polyethylene (PE) (such as high density polyethylene (HDPE), low density polyethylene (LDPE), ultra-low density polyethylene, linear low density polyethylene (LLDPE), or ultra-high molecular weight polyethylene), a polypropylene (PP) (such as isotactic polypropylene, syndiotactic polypropylene, or atactic polypropylene), ethylene-propylene copolymers, polymethylpentene, polybutene-1,1, 2-polybutadiene and other polyolefin resins, polyethylene terephthalate, polybutylene terephthalate, polyethylene naphthalate, and more preferably polyethylene or polypropylene.

There are no particular restrictions on the shape of the container. However, tube, jar, spray can, mist spray bottle, drop container, roll-on container, or a stick-type container is preferred.

Production Method

A topical composition of the present invention can be produced using any method common in the art. If necessary, a sterilization step and a filtration step can be included.

Stratum Corneum Permeation Promoter

The present invention also relates to a stratum corneum permeation promoter for (A) one antifungal agent or two or more antifungal agents selected from the group consisting of tolnaftate and pharmaceutically acceptable salts thereof, the promoter containing (B) at least one compound selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters. The same conditions for the topical composition of the present invention, such as the concentrations of each component, the pH, the hardness, and the formulation conditions, can be adopted for this stratum corneum permeation promoter.

Method for Improving the Amount of Permeation in the Stratum Corneum

The present invention also relates to a method for improving the amount of permeation in the stratum corneum of a subject of tolnaftate and/or a pharmaceutically acceptable salt thereof in a composition, the method comprising applying to the stratum corneum of the subject the composition comprising component (A) in the copresence of (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters. The same conditions for the topical composition of the present invention, such as the concentrations of each component, the pH, the hardness, and the formulation conditions, can be adopted for this stratum corneum permeation promoter. The subject can be, for example, a human subject.

Method for Treating a Fungal Infection of the Stratum Corneum

The present invention also relates to a method for treating a fungal infection of the stratum corneum of a subject in need thereof by applying to the stratum corneum of the subject a topical composition comprising: (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters. Here, the concept of treatment includes not only completely eliminating symptoms but also alleviating symptoms and preventing the worsening of symptoms. The subject can be, for example, a human subject. The same conditions for the topical composition of the present invention, such as the concentrations of each component, the pH, the hardness, and the formulation conditions, can be adopted for this stratum corneum permeation promoter.

Use of a Topical Composition in the Production of a Therapeutic Agent for Fungal Infections of the Stratum Corneum The present invention also relates to a use of a topical composition in the production of a therapeutic agent for fungal infections of the stratum corneum, the topical composition comprising: (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters to produce a therapeutic medicine for a fungal infection of the stratum corneum. The same conditions for the topical composition of the present invention, such as the concentrations of each component, the pH, the hardness, and the formulation conditions, can be adopted for this stratum corneum permeation promoter.

The present invention provides the following.

[1] A topical composition comprising:
(A) one antifungal agent or two or more antifungal agents selected from the group consisting of tolnaftate and pharmaceutically acceptable salts thereof; and
(B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

[2] The topical composition according to [1], further comprising (C) urea.

[3] The topical composition according to [1] or [2], further comprising (D) a dicarboxylic acid ester.

[4] The topical composition according to any one of [1] to [3], wherein the amount of component (A) is from 0.01 to 10 mass % based on the total amount of the composition.

[5] The topical composition according to any one of [1] to [4], wherein the amount of component (B) is from 0.01 to 20 mass % based on the total amount of the composition.

[6] The topical composition according to any one of [1] to [5], wherein the content ratio of component (B) to component (A) is from 0.001 to 200 parts by mass of component (B) per 1 part by mass of component (A).

[7] The topical composition according to any one of [1] to [6], wherein the topical composition is an aqueous composition.

[8] The topical composition according to any one of [1] to [7], wherein the application site is the skin.

[9] The topical composition according to any one of [1] to [8], wherein the application site is the heel.

[10] The topical composition according to any one of [2] to [9], wherein the amount of component (C) is from 0.1 to 40 mass % based on the total amount of the composition.

[11] The topical composition according to any one of [3] to [10], wherein the amount of component (D) is from 0.01 to 40 mass % based on the total amount of the composition.

[12] A method for improving the amount of permeation in the stratum corneum of a subject of (A) tolnaftate and/or a pharmaceutically acceptable salt thereof in a composition, the method comprising applying to the stratum corneum of the subject the composition comprising component (A) in the copresence of (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

[13] A method for treating a fungal infection of the stratum corneum of a subject in need thereof by applying to the stratum corneum of the subject a topical composition comprising: (A) one antifungal agent or two or more antifungal agents selected from the group consisting of tolnaftate and pharmaceutically acceptable salts thereof; and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters.

[14] A use of a topical composition in the production of a therapeutic agent for fungal infections of the stratum corneum, the topical composition comprising: (A) one antifungal agent or two or more antifungal agents selected from the group consisting of tolnaftate and pharmaceutically acceptable salts thereof, and (B) one compound or two or more compounds selected from the group consisting of ester compounds of fatty acids having from 8 to 18 carbon atoms and dihydric alcohols having from 2 to 4 carbon atoms, lysine acyl glutamate, lysine diacyl glutamate, pharmaceutically acceptable salts of lysine acyl glutamate or lysine diacyl glutamate, diethylene glycol-based glycol ethers, cyclohexanedicarboxylic acid polyoxyethylene alkyl ethers, mannosylerythritol lipids, and sucrose fatty acid esters to produce a therapeutic medicine for a fungal infection of the stratum corneum.

[15] The use according to [14], further comprising (C) urea.

[16] The use according to [14] or [15], further comprising (D) a dicarboxylic acid ester.

[17] The use according to any one of [14] to [16], wherein the amount of component (A) is from 0.01 to 10 mass % based on the total amount of the composition.

[18] The use according to any one of [14] to [17], wherein the amount of component (B) is from 0.01 to 20 mass % based on the total amount of the composition.

[19] The use according to any one of [14] to [18], wherein the content ratio of component (B) to component (A) is from 0.001 to 200 parts by mass of component (B) per 1 part by mass of component (A).

[20] The use according to any one of [14] to [19], wherein the topical composition is an aqueous composition.

[21] The use according to any one of [14] to [20], wherein the application site is the skin.

[22] The use according to any one of [14] to [21], wherein the application site is the heel.

[23] The use according to any one of [15] to [22], wherein the amount of component (C) is from 0.1 to 40 mass % based on the total amount of the composition.

[24] The use according to any one of [16] to [23], wherein the amount of component (D) is from 0.01 to 40 mass % based on the total amount of the composition.

EXAMPLES

The present invention will now be described in detail using examples. However, the present invention is not limited to these examples. The numerical values in the tables are all mass % unless otherwise indicated.

Raw Materials Used

The raw materials used in the test examples and formulation examples below are as follows.

Diethylene glycol monoethyl ether: Transcutol CG (made by Gattefosse Corp.)

Bis-ethoxydiglycol cyclohexane dicarboxylate: Neosolue Aqulio (made by Nippon Fine Chemical Co., Ltd.)

Propylene glycol monocaprylate: Capryol™ 90 (made by Gattefosse Corp.)

Sodium dilauramidoglutamide lysine: Pelicer L-30 (made by Asahi Kasei Finechem Co., Ltd.)

Mannosylerythritol lipids: Ceramela-HG (made by Toyobo Co., Ltd.)

Sucrose lauric acid ester (HLB1): RYOTO™ SUGAR ESTER L-195 (HLB=1) (made by Mitsubishi Chemical Foods Co., Ltd.)

Sucrose lauric acid ester (HLB5): RYOTO™ SUGAR ESTER L-595 (HLB=5) (made by Mitsubishi Chemical Foods Co., Ltd.)

Sucrose lauric acid ester (HLB16): RYOTO™ SUGAR ESTER L-1695 (HLB=16) (made by Mitsubishi Chemical Foods Co., Ltd.)

Test Example 1. Permeability Test 1

The topical compositions shown in TABLES 1-6 below were prepared in the usual manner. The topical compositions were then subjected to a permeability test. This test was conducted and the calculations performed using in-vitro skin absorption testing method OECD TG428 (Skin Absorption. In vitro Method, adopted Apr. 13, 2004) in accordance with the guidelines for chemical testing from the Organization for Economic Co-operation and Development (OECD).

More specifically, each composition was prepared in the usual manner in accordance with TABLES 1-6, and the amount of permeation by tolnaftate in the compositions under infinite dosing was measured and confirmed using a Franz Cell (PermeGear, Inc., jacketed stationary type, flat jacket with a 9 mm clearance, 5 ml, 0.64 square cm transmission area). A reservoir solution was prepared (0.1 (w/v) % polyethylene glycol monooleyl ether (20 E.O.) in PBS), and the receptor compartment was filled with 5 mL of the reservoir solution, which was stirred for 30 minutes. A piece of skin (Yucatan Micropig, about 700 μm) was interposed between the Franz Cell and a ground glass donor and fixed. The constant temperature bath was set to 32° C., and the constant temperature bath and the Franz Cell were connected so that the reservoir solution was kept at a constant temperature. Twenty-four hours after the start of stirring, the Franz Cell was disassembled, the skin was removed, and any formulation remaining on the skin was washed away. The skin was homogenized, the reservoir solution was collected, and the amount of tornafate in the skin (horny layer, epidermis, dermis) and in the reservoir solution was measured by HPLC. The components were detected using an ultraviolet absorptiometer at a wavelength of 257 nm, and the amount (permeating amount) of tornafate in the skin (horny layer, epidermis, dermis) and in the reservoir solution was calculated from the calibration curves for the components. The improvement in permeability for each composition was calculated using Equation (1) below. The "corresponding reference example" in the equation is the reference example with the same number as the example. For example, the reference example for Example 1 is Reference Example 1. The test results are shown in TABLES 1-6.

Improvement in Permeability (%)=(permeating amount in the example/permeating amount in the corresponding reference example−1)×100 (1)

TABLE 1

Compositions Ref. Ex. 1, Ex. 1-1, and Ex. 1-2.

| Ingredient Name | Ref. Ex. 1 | Ex. 1-1 | Ex. 1-2 |
|---|---|---|---|
| Tolnaftate | 1 | 1 | 1 |
| Diethylene Glycol Monoethyl Ether | — | 2.6 | — |
| Bis-Ethoxydiglycol Cyclohexane Dicarboxylate | — | — | 5 |
| PEG 400 | Bal. | Bal. | Bal. |
| Total | 100 | 100 | 100 |
| Improvement in Permeability (%) | — | 87.2 | 299.4 |

TABLE 2

Compositions Ref. Ex. 1 and Ex. 1-3.

| Ingredient Name | Ref. Ex. 1 | Ex. 1-3 |
|---|---|---|
| Tolnaftate | 1 | 1 |
| Propylene Glycol Monocaprylate | — | 1 |
| PEG 400 | Bal. | Bal. |
| Total | 100 | 100 |
| Improvement in Permeability (%) | — | 283.7 |

TABLE 3

Compositions Ref. Ex. 1, Ex. 1-4, Ex. 1-5, Ex. 1-6, Ex. 1-7, and Ex. 1-8.

| Ingredient Name | Ref. Ex. 1 | Ex. 1-4 | Ex. 1-5 | Ex. 1-6 | Ex. 1-7 | Ex. 1-8 |
|---|---|---|---|---|---|---|
| Tolnaftate | 1 | 1 | 1 | 1 | 1 | 1 |
| Sodium Dilauramidoglutamide Lysine | — | 1 | — | — | — | — |
| Mannosylerythritol Lipids | — | — | 1 | — | — | — |
| Sucrose Lauric Acid Ester (HLB1) | — | — | — | 1 | — | — |
| Sucrose Lauric Acid Ester (HLB5) | — | — | — | — | 1 | — |
| Sucrose Lauric Acid Ester (HLB16) | — | — | — | — | — | 1 |
| PEG 400 | Bal. | Bal. | Bal. | Bal. | Bal. | Bal. |
| Total | 100 | 100 | 100 | 100 | 100 | 100 |
| Improvement in Peimeability (%) | — | 127.8 | 60.8 | 108.9 | 179.2 | 44.0 |

TABLE 4

Compositions Ref. Ex. 2, Ex. 2-1, Ex. 2-2, and Ex. 2-3.

| Ingredient Name | Ref. Ex. 2 | Ex. 2-1 | Ex. 2-2 | Ex. 2-3 |
|---|---|---|---|---|
| Tolnaftate | 1 | 1 | 1 | 1 |
| Bis-Ethoxydiglycol Cyclohexane Dicarboxylate | — | 1 | 3 | 5 |
| Urea | 10 | 10 | 10 | 10 |
| Conc. Glycerin | 5 | 5 | 5 | 5 |
| Squalene | 5 | 5 | 5 | 5 |
| Caprylic/Capric Triglyceride | 7 | 7 | 5 | 3 |
| Jojoba Oil | 5 | 5 | 5 | 5 |
| Beeswax | 4 | 4 | 4 | 4 |
| Cetanol | 4 | 4 | 4 | 4 |
| Triethanolamine | 0.6 | 0.6 | 0.6 | 0.6 |
| Thickener (Carbomer) | 0.5 | 0.5 | 0.5 | 0.5 |
| Surfactants (Sorbitan Monostearate, Polyoxyethylene Cetyl Ether) | 2.7 | 2.7 | 2.7 | 2.7 |
| Purified Water | Bal. | Bal. | Bal. | Bal. |
| Total | 100 | 100 | 100 | 100 |
| pH | 7.8 | 6.8 | 6.8 | 6.7 |
| Improvement in Permeability (%) | — | 31.3 | 64.2 | 42.3 |

TABLE 5

Compositions Ref. Ex. 3 and Ex. 3.

| Ingredient Name | Ref. Ex. 3 | Ex. 3 |
|---|---|---|
| Tolnaftate | 1 | 1 |
| Diethylene Glycol Monoethyl Ether | — | 1.25 |
| Propylene Glycol Monocaprylate | — | 0.5 |
| Sodium Dilauramidoglutamide Lysine | — | 0.1 |
| Urea | 10 | 10 |
| Diethyl Sebacate | — | 1 |
| Conc. Glycerin | 5 | 5 |
| Squalene | 10.5 | 9 |
| Cetanol | 5 | 5 |
| Medium-Chain Fatty Acid Triglyceride | 8 | 8 |
| Jojoba Oil | 7 | 7 |
| Triethanolamine | 0.3 | 0.3 |
| Viscosity Modifiers (Carboxyvinyl Polymer, Hydroxyethyl Cellulose) | 0.4 | 0.4 |

TABLE 5-continued

Compositions Ref. Ex. 3 and Ex. 3.

| Ingredient Name | Ref. Ex. 3 | Ex. 3 |
|---|---|---|
| Surfactants (Sorbitan Monostearate, Polyoxyethylene Cetyl Ether) | 2.7 | 2.7 |
| Purified Water | Bal. | Bal. |
| Total | 100 | 100 |
| pH | 8.2 | 6.7 |
| Improvement in Permeability (%) | — | 62.5 |

TABLE 6

Compositions Ref. Ex. 4 (commercial cream), Ex. 4-1, and Ex. 4-2.

| Ingredient Name | Ref. Ex. 4 (Commercial Cream) | Ex. 4-1 | Ex. 4-2 |
|---|---|---|---|
| Tolnaftate | 1 | 1 | 1 |
| Diethylene Glycol Monoethyl Ether | — | 1.25 | 2.50 |
| Propylene Glycol Monocaprylate | — | 0.5 | 0.5 |
| Sodium Dilauramidoglutamide Lysine | — | 0.1 | 0.1 |
| Urea | — | 10 | 10 |
| Diethyl Sebacate | — | 1 | 1 |
| Conc. Glycerin | — | 5 | 5 |
| Squalene | — | 9 | 9 |
| Cetanol | — | 5 | 5 |
| Medium-Chain Fatty Acid Triglyceride | — | 8 | 8 |
| Jojoba Oil | — | 7 | 7 |
| Triethanolamine | — | 0.3 | 0.3 |
| Viscosity Modifiers (Carboxyvinyl Polymer, Hydroxyethyl Cellulose) | — | 0.4 | 0.4 |
| Surfactants (Sorbitan Monostearate, Polyoxyethylene Cetyl Ether) | — | 2.7 | 2.7 |
| Ceteth-20 | Amount not disclosed | — | — |
| Cetostearyl Alcohol | Amount not disclosed | — | — |
| Chlorocresol | Amount not disclosed | — | — |
| Mineral Oil | Amount not disclosed | — | — |
| Propylene Glycol | Amount not disclosed | — | — |
| Monosodium Phosphate | Amount not disclosed | — | — |
| White Petrolatum | Amount not disclosed | — | — |
| Purified Water | Amount not disclosed | Bal. | Bal. |
| Total | 100 | 100 | 100 |
| pH | — | 6.7 | 8.2 |
| Improvement in Permeability (%) | — | 83.3 | 196.2 |

The results of testing confirmed that the permeability of component (A) is improved by the copresence of component (A) and component (B) in the compositions in the examples. Note that no tolnaftate was detected in the dermis and in the reservoir fluid when the skin pieces after the testing shown in Table 1 were divided into horny layer/epidermis and dermis, and the amounts of tolnaftate present in each layer of the skin pieces and in the reservoir solution were quantified. These results confirm that the examples are very safe formulations that suppress permeation into the deeper layers of the skin.

Test Example 2. Permeability Test 2

For the topical compositions shown in TABLES 7-8, the permeating amount of tolnaftate was calculated using the same procedure as in Test Example 1, and the improvement in permeability was calculated using Equation (1). The "corresponding reference example" in the equation is the reference example with the same number as the comparative examples. For example, the reference example for Comparative Example 5-1 is Reference Example 5. The test results are shown in TABLES 7-8.

TABLE 7

Compositions Ref. Ex. 5, C. Ex. 5-1, C. Ex. 5-2, and C. Ex. 5-3.

| Ingredient Name | Ref. Ex. 5 | C. Ex. 5-1 | C. Ex. 5-2 | C. Ex. 5-3 |
|---|---|---|---|---|
| Tolnaftate | 1 | 1 | 1 | 1 |
| Isopropyl Lauroyl Sarcosinate | — | 5 | — | — |
| (Eicosane Diacid/Tetradecane Diacid) | — | — | 5 | — |
| Polyglyceryl-10 Dimethyl Isosorbide | — | — | — | 5 |
| PEG 400 | Bal. | Bal. | Bal. | Bal. |
| Total | 100 | 100 | 100 | 100 |
| Improvement in Permeability (%) | — | −50.3 | −13.0 | −2.2 |

TABLE 8

Compositions Ref. Ex. 5 and C. Ex. 5-4.

| Ingredient Name | Ref. Ex. 5 | C. Ex. 5-4 |
|---|---|---|
| Tolnaftate | 1 | 1 |
| Isopropyl Myristate | — | 5 |
| PEG 400 | Bal. | Bal. |
| Total | 100 | 100 |
| Improvement in Permeability (%) | — | −3.5 |

The permeability in the compositions of the comparative examples was lower than that of the reference examples. Even though generally known to be permeability improving components, the components did not improve the permeability of tolnaftate but instead decreased it.

Test Example 3. Permeability Test 3

For the topical compositions shown in TABLE 9, the permeating amount of tolnaftate was calculated using the same procedure as in Test Example 1, and the improvement in permeability of each composition was calculated using Equation (1). The "corresponding reference example" in the equation is the reference example with the same number as the examples. For example, the reference example for Example 6-1 is Reference Example 6. The test results are shown in TABLE 9.

TABLE 9

Compositions Ref Ex. 6, Ex. 6, Ref Ex. 7, and Ex. 7.

| Ingredient Name | Ref. Ex. 6 | Ex. 6 | Ref. Ex. 7 | Ex. 7 |
|---|---|---|---|---|
| Tolnaftate | 0.1 | 0.1 | 3 | 3 |
| Propylene Glycol Monocaprylate | — | 5.0 | — | 0.1 |
| Sodium Dilauramido glutamide Lysine | — | 0.01 | — | 1 |
| Urea | 5 | 5 | 20 | 20 |
| Diethyl Sebacate | — | 0.5 | — | 10 |
| Conc. Glycerin | 5 | 5 | 5 | 5 |
| Squalene | 9 | 9 | 6 | 6 |
| Cetanol | 5 | 5 | 5 | 5 |

TABLE 9-continued

Compositions Ref Ex. 6, Ex. 6, Ref Ex. 7, and Ex. 7.

| Ingredient Name | Ref. Ex. 6 | Ex. 6 | Ref. Ex. 7 | Ex. 7 |
|---|---|---|---|---|
| Medium-Chain Fatty Acid Triglyceride | 5 | 5 | 4 | 4 |
| Jojoba Oil | 4.5 | 4.5 | 3 | 3 |
| Triethanolamine | 0.3 | 0.3 | 0.3 | 0.3 |
| Viscosity Modifiers (Carboxyvinyl Polymer, Hydroxyethyl Cellulose) | 0.4 | 0.4 | 0.4 | 0.4 |
| Surfactants (Sorbitan Monostearate, Polyoxyethylene Cetyl Ether) | 2.7 | 2.7 | 2.7 | 2.7 |
| Purified Water | Bal. | Bal. | Bal. | Bal. |
| Total | 100 | 100 | 100 | 100 |
| pH | 7.5 | 7.2 | 7.7 | 6.9 |
| Improvement in Permeability (%) | — | 218.5 | — | 839.2 |

Test Example 4. Subjective Testing

The topical compositions shown in TABLE 10 were prepared for use as test samples. The subjective quality was evaluated for each test sample. Specifically, the forearms of the subjects (five healthy subjects) were washed and dried five minutes before the test. A 0.1 g test sample was scooped with a spatula and spread with the fingers on the forearm. Spreadability of the formulations on the skin was evaluated at the time of application and five minutes after application using the visual analog scale (VAS) method. The length of the 100 cm line segment from the left end to the position of the diagonal line used to answer each question was measured and used as the value for the answer. "Very difficult to spread" was the worst situation at 0 and "easy to spread" was the best situation at 100. The test was conducted so that the details for each formulation could not be identified by the subjects. The rate of improvement (%) in the score for each example relative to the corresponding reference example was calculated from the resulting VAS scores using Equation (2) below, and the result was used as the rate of improvement. The "corresponding reference example" in the equation is the reference example with the same number as the examples. For example, the reference example for Comparative Example 8-1 is Reference Example 8. The evaluation results from the subjective testing are shown in Table 10.

Rate of improvement (%)={(average value of the VAS score for the example/average value of the VAS score for the corresponding reference example)−1}×100     (2)

TABLE 10

Evaluation results from subjective testing.

| Ingredient Name | Ref. Ex. 8 | Ex. 8-1 | Ex. 8-2 | Ref. Ex. 9 | Ex. 9 |
|---|---|---|---|---|---|
| Tolnaftate | 1 | 1 | 1 | 0.1 | 0.1 |
| Diethylene Glycol Monoethyl Ether | — | 1.25 | 2.5 | — | — |
| Propylene Glycol Monocaprylate | — | 0.5 | 0.5 | — | 5 |
| Sodium Dilauramidoglutamide Lysine | — | 0.1 | 0.1 | — | 0.01 |
| Urea | 10 | 10 | 10 | 5 | 5 |
| Diethyl Sebacate | — | 1 | 1 | — | 0.5 |
| Conc. Glycerin | 5 | 5 | 5 | 5 | 5 |
| Squalene | 10.5 | 9 | 9 | 9 | 9 |
| Cetanol | 5 | 5 | 5 | 5 | 5 |
| Medium-Chain Fatty Acid Triglyceride | 8 | 8 | 8 | 5 | 5 |
| Jojoba Oil | 7 | 7 | 7 | 4.5 | 4.5 |
| Triethanolamine | 0.3 | 0.3 | 0.3 | 0.3 | 0.3 |
| Viscosity Modifiers (Carboxyvinyl Polymer, Hydroxyethyl Cellulose) | 0.4 | 0.4 | 0.4 | 0.4 | 0.4 |
| Surfactants (Sorbitan Monostearate, Polyoxyethylene Cetyl Ether) | 2.7 | 2.7 | 2.7 | 2.7 | 2.7 |
| Purified Water | Bal. | Bal. | Bal. | Bal. | Bal. |
| Total | 100 | 100 | 100 | 100 | 100 |
| pH | 8.2 | 6.7 | 8.2 | 7.5 | 7.2 |
| Improvement in Spreading During Application | — | 26.3 | 28.5 | — | 179.5 |
| Improvement in Spreading 5 Min. After Application (%) | — | 37.1 | 46.2 | — | 62.9 |

Compared to the reference examples, the rate of improvement for the examples was significant. Because the formulations of the present invention spread well and can be applied easily to the affected area, highly effective formulations can be expected Formulations of the present invention are shown below. Compositions for topical use were prepared in the usual manner according to the formulations shown in TABLES 11-12. These formulations can be effectively used on skin symptoms caused by *Trichophyton*. After preparation, Formulations 6 and 7 were used to fill roll-on containers and mist containers, respectively. After preparation, Formulations 8 and 9 were used as a liquid solution with gas to fill containers for aerosol preparations and obtain aerosol preparations (total amount 400 g).

TABLE 11

Compositions Form. 1, Form. 2, Form. 3, Form. 4, Form. 5, Form. 6, and Form 7.

| Ingredient Name | Form. 1 Cream | Form. 2 Cream | Form. 3 Cream | Form. 4 Cream | Form. 5 Cream | Form. 6 Liquid | Form. 7 Liquid |
|---|---|---|---|---|---|---|---|
| Tolnaftate | 0.5 | 1 | 1 | 2 | 3 | 1 | 1 |
| Diethylene Glycol Monoethyl Ether | 2.6 | 1 | — | 2 | 5 | 3 | — |
| Propylene Glycol Monocaprylate | 3 | 5 | — | 0.5 | 0.5 | — | 0.5 |
| Propylene Glycol Dicaprylate | — | 2 | — | — | — | — | — |

TABLE 11-continued

Compositions Form. 1, Form. 2, Form. 3, Form. 4, Form. 5, Form. 6, and Form 7.

| Ingredient Name | Form. 1 Cream | Form. 2 Cream | Form. 3 Cream | Form. 4 Cream | Form. 5 Cream | Form. 6 Liquid | Form. 7 Liquid |
|---|---|---|---|---|---|---|---|
| Sodium Dilauramidoglutamide Lysine | 0.3 | — | 0.8 | 0.5 | 0.1 | — | 0.3 |
| Bis-Ethoxydiglycol Cyclohexane Dicarboxylate | — | 3 | — | 8 | 1 | 5 | — |
| Mannosylerythritol Lipids | 0.1 | — | 0.5 | — | — | — | 0.2 |
| Sucrose Lauric Acid Ester (HLB5) | 0.8 | — | 0.8 | — | — | 0.3 | — |
| Urea | 10 | 5 | 20 | 15 | 10 | — | — |
| Diethyl Sebacate | 5 | — | 0.5 | 1 | — | — | 1 |
| Diisopropyl Adipate | — | 1 | 0.5 | — | 1 | — | — |
| Conc. Glycerin | — | 5 | 3 | 5 | 3 | 2 | 3 |
| 1,3-Butylene Glycol | 5 | — | — | — | 3 | — | — |
| Squalene | 5 | 5 | — | 10 | 5 | — | — |
| Liquid Paraffin | — | 5 | 10 | — | 5 | — | — |
| Paraffin | 2 | — | — | — | 1 | — | — |
| Ceresin | — | — | 0.5 | — | — | — | — |
| Microcrystalline Wax | 1 | — | — | — | 1 | — | — |
| Dimethicone | 0.3 | — | — | — | — | — | — |
| Cetanol | 3 | — | 1 | 5 | 3 | — | — |
| Medium-Chain Fatty Acid Triglyceride | 10 | 8 | — | 7 | 5 | — | — |
| Jojoba Oil | — | 4 | 8 | 3 | 7 | 0.3 | — |
| Sweet Almond Oil | 5 | 4 | 8 | 3 | — | — | 0.3 |
| Triethanolamine | 0.3 | 0.3 | 0.4 | 0.3 | 0.3 | — | — |
| Viscosity Modifiers (Carboxyvinyl Polymer, Hydroxyethyl Cellulose) | 0.3 | 0.4 | 0.5 | 0.4 | 0.4 | 0.2 | 0.3 |
| Surfactants (Sorbitan Monostearate, Polyoxyethylene Cetyl Ether) | 1.9 | 2.7 | 1.9 | 2.7 | 2.7 | — | — |
| Silicic Anhydride | 0.3 | — | — | — | — | 3 | 2 |
| Ethanol | — | — | — | — | — | 50 | 60 |
| Purified Vater | Bal. | Bal. | Bal. | Bal. | Bal. | Bal. | Bal. |
| Total | 100 | 100 | 100 | 100 | 100 | 100 | 100 |

TABLE 12

Compositions Form. 8 and Form. 9.

| Ingredient Name | Form. 8 Aerosol | Form. 9 Aerosol |
|---|---|---|
| Tolnaftate | 4 | 4 |
| Diethylene Glycol Monoethyl Ether | 4 | 8 |
| Sodium Dilauramidoglutamide Lysine | 0.4 | — |
| Bis-Ethoxydiglycol Cyclohexane Dicarboxylate | 1 | — |
| Mannosylerythritol Lipids | — | 0.4 |
| Sucrose Lauric Acid Ester (HLB5) | — | 0.4 |
| Diethyl Sebacate | 12 | — |
| Silicic Anhydride | 8 | 12 |
| Ethanol | Bal. | Bal. |
| Dimethyl Ether | 300 | 300 |
| Total | 400 | 400 |

The invention claimed is:

1. A topical composition comprising:
(A) tolnaftate ("component (A)");
(B) propylene glycol monocaprylate ("component (B-1)"); and
(C) urea ("component (C)"), wherein:
the topical composition is an emulsion;
the component (A) and the component (B-1) have been mixed within the emulsion independently of each other;
the content ratio of component (B-1) to component (A) is from 0.5 to 5 parts by mass of component (B-1) per 1 part by mass of component (A); and
the amount of component (A) is 1 mass % based on the total amount of the topical composition.

2. The topical composition according to claim 1, further comprising (D) a dicarboxylic acid ester.

3. The topical composition according to claim 1, wherein the topical composition is an aqueous composition.

4. A method for improving the amount of permeation of tolnaftate in the stratum corneum of a subject, the method comprising applying to the stratum corneum of the subject the topical composition according to claim 1.

5. The method according to claim 4, wherein the topical composition is applied at skin of the subject.

6. The method according to claim 4, wherein the topical composition is applied at a heel of the subject.

7. A method for treating a fungal infection of the stratum corneum of a subject in need thereof by applying to the stratum corneum of the subject the topical composition according to claim 1, wherein the fungal infection is selected from one or more of athlete's foot, ringworm, candidiasis, and *tinea versicolor*.

8. The method according to claim 7, wherein the topical composition is applied at skin of the subject.

9. The method according to claim 7, wherein the topical composition is applied at a heel of the subject.

10. The topical composition according to claim 1, further comprising 15-75 mass % water.

11. The topical composition according to claim 1, wherein the content ratio of (A) to (C) is 0.7 to 170 parts by mass of component (A) per 1 part by mass of component (C).

12. The topical composition according to claim 1, wherein the amount of component (C) is 0.5-30 mass % based on the total amount of the topical composition.

* * * * *